United States Patent [19]

Schmidberger

[11] 4,351,182
[45] Sep. 28, 1982

[54] OXYGEN SENSOR FOR MONITORING EXHAUST GASES

[75] Inventor: Rainer Schmidberger, Bermatingen, Fed. Rep. of Germany

[73] Assignee: Dornier System GmbH, Friedrichshafen, Fed. Rep. of Germany

[21] Appl. No.: 134,123

[22] Filed: Mar. 26, 1980

[30] Foreign Application Priority Data

Apr. 21, 1979 [DE] Fed. Rep. of Germany ....... 2916178

[51] Int. Cl.³ ............................................. G01N 27/12
[52] U.S. Cl. .................................... 73/27 R; 338/34; 422/98
[58] Field of Search ................... 73/23, 27 R; 422/98; 431/13; 338/34

[56] References Cited

U.S. PATENT DOCUMENTS

| 3,340,014 | 9/1967 | Neal et al. | 422/98 |
| 3,426,579 | 2/1969 | Lebel et al. | 73/23 |
| 3,865,550 | 2/1975 | Bott et al. | 73/23 R X |
| 4,193,965 | 3/1980 | Cullingford et al. | 73/23 R X |

Primary Examiner—James J. Gill
Attorney, Agent, or Firm—Marianne Rich

[57] ABSTRACT

A sensor measuring the partial oxygen pressure in furnace exhaust gas has an active layer of palladium. When the sensor is maintained at a particular temperature, for example about 700° C., the palladium changes to palladium oxide at a specific air number, namely 1.2. The change from palladium to palladium oxide and vice versa causes a change in conductivity by a factor of approximately 20. This change in conductivity is a clearly defined output signal which can be adjusted to occur at any desired air number in the region from 1.05-1.4, depending upon the temperature at which the sensor is maintained. Two sensors may be used, each maintained at a different temperature so that a control region is defined as the air number region wherein the sensor maintained at the lower temperature is oxidized while the second sensor is reduced. Preferably, the active layer consists not only of the metal oxide but also of a ceramic component such as cerium oxide which is doped with 0.5-10% by volume of $Nb_2O_5$ or $Ta_2O_5$.

12 Claims, 3 Drawing Figures

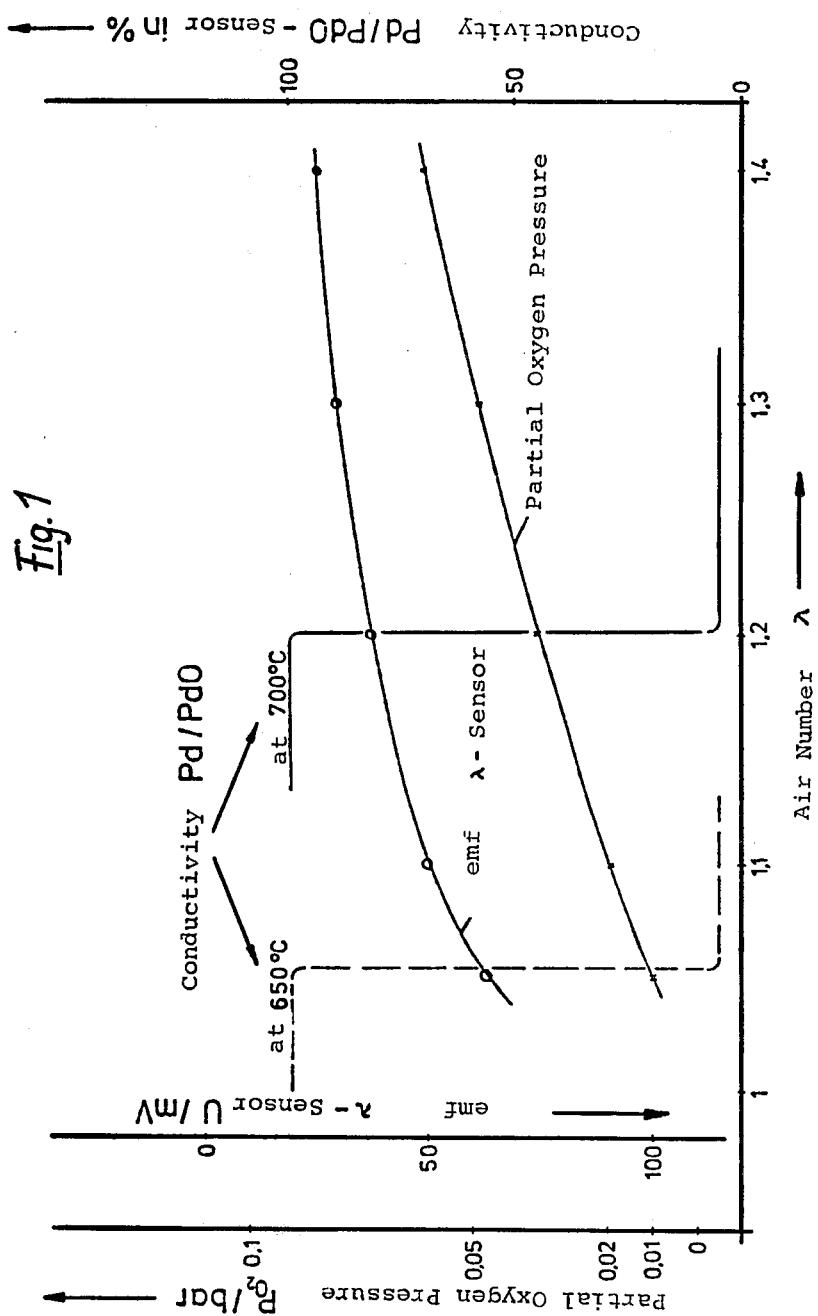

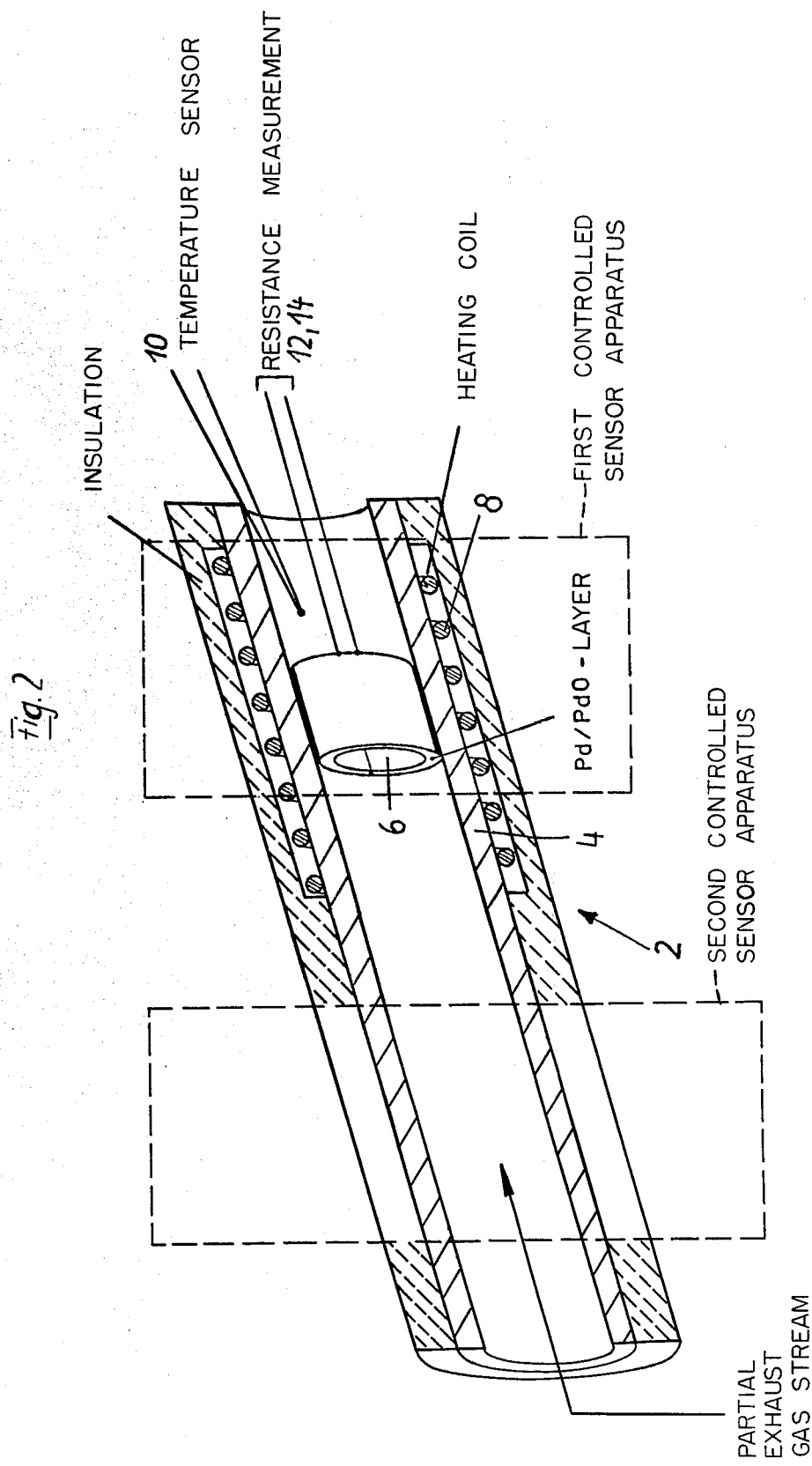

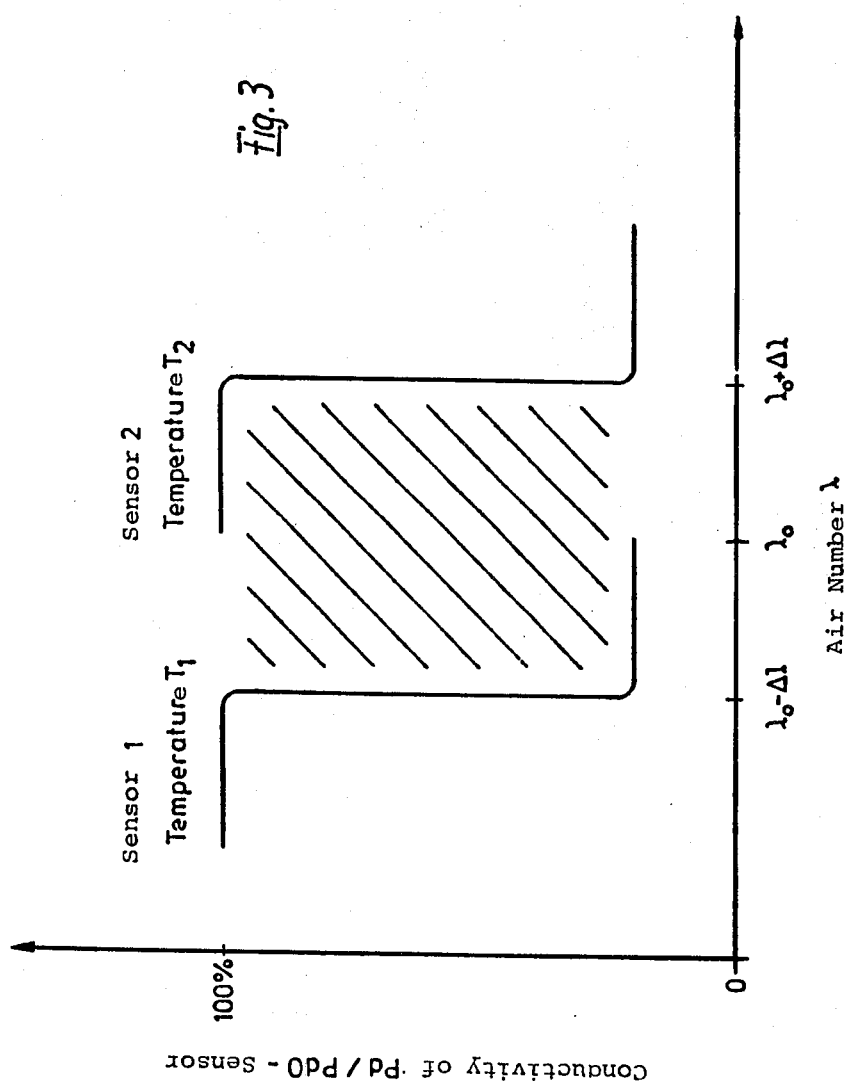

OXYGEN SENSOR FOR MONITORING EXHAUST GASES

The present invention relates to sensors which sense the partial pressure of oxygen in a gas mixture. In particular, it concerns sensors which are used in systems monitoring the exhaust gases from furnaces.

BACKGROUND AND PRIOR ART

The optimum functioning of a furnace can be considered from two points of view, namely from the point of view of fuel consumption and from the point of view of emission of noxious gases.

In order to meet legal requirements regarding the maximum allowable emission of noxious gases or pollutants and, at the same time, to maximize the use of fuel, furnaces must be operated with excess air of between 5% and 40% (air number $\lambda = 1.05$–$1.4$), the optimum value depending upon the type of furnace and boiler used.

However, the air excess should not exceed that which is absolutely essential, since increases in excess air, while decreasing the emission of pollutants, at the same time decrease the efficiency of the furnace since a greater amount of ballast air must be warmed and discharged through the chimney.

The partial pressure of oxygen in the exhaust gases is determined by the amount of excess air during combustion. The higher the excess air, that is the higher the amount of air relative to that required for complete combustion, the larger the partial pressure of oxygen in the exhaust gases.

The amount of excess air during combustion can thus be monitored for purposes of control and regulation of the operating conditions of the furnace by measuring the partial pressure of oxygen in the exhaust gases.

This principle has been used for several applications, sensors having been developed in particular for monitoring the emission of pollutants of internal combustion engines by measuring the partial oxygen pressure in the exhaust gases of automobiles.

In automobiles, a closed loop control circuit is provided which utilizes the sensor output to stablize the air-fuel mixture to the value $\lambda = 1$, since, for a stoichiometric air/fuel ratio an almost complete elimination of pollutants can be accomplished by a subsequent catalytic converter. For a gas mixture in thermodynamic equilibrium, the partial oxygen pressure in the exhaust gas at $\lambda = 1$ changes abruptly by several factors of ten. The associated jump in the signal furnished by the sensor allows a relatively simple electronic regulation of the air/fuel ratio to the value $\lambda = 1$.

Since, for furnaces, no catalytic after-reaction of the exhaust gases takes place, the combustion should be carried out with an air number $\lambda > 1$ to minimize the emission of pollutants.

These relationships are published in a number of publications. In the Motortechnischen Zeitschrift 34 (1973) 1, S. 7, R. Zechnall and G. Baumann give a general overview of the purifying of exhaust gases of Otto motors. Closed loop control circuits are used. The sensors are so-called $\lambda$ sensors which generate a voltage which varies as a function of the partial pressure of oxygen in the exhaust gas. The basic operating principle of such a sensor includes the comparision of the partial oxygen pressure in the exhaust gas and that in the surrounding air by means of a solid electrolyte (zirconium dioxide) which is conductive to oxygen ions and which separates the two gases from each other. Electrodes are affixed to the electrolyte and a so-called Nernst voltage is generated between the electrodes which varies as a function of the partial pressure of oxygen on each side. It also depends upon the temperature at which the sensor is maintained. The output voltage of such a zirconium dioxide sensor undergoes a rapid change at the value $\lambda = 1$, while the variation as a function of partial oxygen pressure for $\lambda < 1$ and $\lambda > 1$ is very small.

A further principle for monitoring the partial oxygen pressure in exhaust gases of automobiles is described by Tien, Stadler, Gibbons and Zacmanidis in Ceramic Bulletin Vol. 54, No. 3 (1975) page 280. Here the quasicontinuous oxygen reduction of $TiO_2$ in dependence of the partial oxygen pressure in the surrounding gaseous atmosphere is used for measuring the partial pressure of oxygen.

Discharge of oxygen causes the electrical conductivity of titanic oxide to change continuously. The variation of resistance of such a sensor as a function of air number $\lambda$ has a similar variation as the voltage of an emf sensor. In particular, the variation of resistance as a function of partial oxygen pressure is very small for $\lambda > 1$.

A similar sensor is described in U.S. Pat. No. 1,467,735.

In known sensors for partial oxygen pressure in flue gas and furnace installations similar sensors to those described in relation to automobiles are used. In the system described in German published application No. DE-AS 2,400,246, a solid electrolyte cell of zirconium oxide is arranged in the stream of the exhaust gas and air is used as a comparison gas. In order that the partial oxygen pressure may be measured by such a sensor, it must be temperature-stablized. For this purpose in the above-mentioned German patent, a heating coil is wound around the sensor. The evaluation and further processing of the output signal of such a sensor is very difficult because of its above-mentioned very small variation as a function of partial oxygen pressure. Published German application No. 2,510,189 describes the use of a zirconium oxide sensor in the flue gas of a furnace for direct control of the burner, that is for regulation of the air/fuel ratio. Such installations have been used in practice, but their application is limited to very large furnaces, since the costs of a control system utilizing zirconium oxide sensors is very high. These high costs are the result of the small variation of output signal of the sensor as a function of partial oxygen pressure, since this leads to very complicated and expensive electronic circuits if the fuel/air ratio is to be stablized within a narrow $\lambda$ region for $\lambda$ values $> 1$.

To overcome these difficulties, attempts have been made to increase the variation of the output signal of the sensor as a function of partial oxygen pressure by adding an auxiliary gas (hydrogen) to the exhaust gas to be monitored. In thermodynamic equilibrium, the addition of the auxiliary gas causes the signal change which otherwise takes place at $\lambda = 1$ to occur at values of $\lambda > 1$. The value of $\lambda$ at which the sudden jump occurs depends upon the ratio of exhaust gas flow to auxiliary gas flow. For this arrangement, the problem of maintaining the ratio of exhaust gas flow to auxiliary gas flow constant requires approximately as much equipment and therefore is of approximately the same cost as the problem of maintaining the air/fuel ratio at the input of the burner constant.

To allow the application of monitoring and control systems for exhaust gas in household furnaces, inexpensive and simple measuring systems must be developed which do not require an auxiliary gas as a reference and whose output signal in the λ region of interest has a strong variation as a function of partial oxygen pressure.

SUMMARY OF THE INVENTION

It is the object of the present invention to develop an oxygen sensor whose output signal has a strong variation as a function of partial oxygen pressure in the region between 0.01 and 0.08 bar, corresponding to a λ region of 1.05–1.4. Further, the sensor according to the present invention is to operate without an auxiliary or reference gas. Its manufacturing costs are to be so low that its use in household furnaces is economically feasible.

In an oxygen sensor according to the present invention, a sudden conversion of metal into a metal oxide in dependence upon the partial oxygen pressure and temperature and the associated change in electrical conductivity is used as the sensor output signal. At any given temperature, the change from metal to metal oxide takes place at a predetermined partial oxygen pressure. For particular metals, this change takes place very suddenly when the solubility of the oxide in the metal is small and the specific surface area of the metal is sufficiently large to allow a rapid exchange of oxygen.

It was found that the metal-metal oxide system comprising palladium-palladium oxide (Pd-PdO) has particularly suitable properties for use as an oxygen sensor in the partial pressure region which is of interest. The change from metal to metal oxide for palladium takes place in a temperature region between 650° and 850° C. for the air number region $\lambda = 1.05$–1.4.

The novel features which are considered as characteristic for the invention are set forth in particular in the appended claims. The invention itself, however, both as to its construction and its method of operation, together with additional objects and advantages thereof will best be understood from the following description of specific embodiments when read in connection with the accompanying drawing.

FIG. 1 shows the variation of output signal of a Pd-PdO sensor in accordance with the present invention as a function of air number λ in comparison to the output signal of an emf sensor used in known systems;

FIG. 2 shows a preferred embodiment of the sensor of the present invention mounted in the stream of exhaust gas; and FIG. 3 is a diagram illustrating the stabilization of the air number to a value $\lambda_0 \pm \Delta\lambda$ using two sensors according to the present invention.

DESCRIPTION OF THE PREFERRED EMBODIMENT

In FIG. 1 the variation of the output signal of a sensor according to the present invention, that is the variation of the conductivity of a Pd-PdO sensor as a function of air number is shown in dashed lines, while the variation of the output signal of a known sensor is shown as a solid line. At the point of discontinuity, the conductivity of the palladium sensor changes by a factor of about 20. In order to decrease the response time of a palladium-palladium oxide sensor as much as possible, the ratio of surface area to volume of active palladium must be as large as possible. This is particularly important for increasing the speed of oxidation, since the latter is decreased considerably by protective passive layers. There is a strong temperature dependence of partial oxygen pressure of palladium oxide. This means that the temperature of the sensor must be stabilized within relatively narrow boundaries. A temperature change of 8° corresponds to a shift in air number of 0.01.

The sensor according to the present invention has a number of advantages insofar as use in furnaces is concerned, relative to the known emf or titanium dioxide sensors. First, the sensor according to the present invention requires no reference or auxiliary gas as do the emf sensors utilizing zirconium oxide. As previously mentioned, the required separation between the exhaust gas and the reference gas creates a problem in the latter systems. A further advantage of the sensor according to the present invention is the sharp discontinuity of the conductivity for a defined partial oxygen pressure, the actual partial pressure at which the discontinuity takes place being dependent only upon the temperature of the sensor. The sensor is thus particularly suitable for controlling the air number to any desired air number by controlling the temperature of the sensor by means of a known closed loop temperature control circuit. Since these circuits can regulate to a desired temperature simply by change of the reference temperature signal applied thereto, the sensor of the present invention can readily be matched to the particular requirements of a given furnace.

FIG. 2 shows a preferred embodiment of the sensor according to the present invention. Sensor 2 consists of a ceramic supporting pipe 4 approximately 5 cm in length and having an outer diameter of approximately 8 mm and an inner diameter of approximately 5 mm. An active palladium layer 6 on the inside of the ceramic tube extends in its central region over a length of 5 mm. The thickness of the palladium layer 6 is for example between 20 and 100 μm. A heating coil 8 is wound around the outside of pipe 4, the temperature of the sensor being sensed in the region of the active layer by a temperature sensing element 10. The temperature sensing element can be any known element, such as, for example, a thermistor. The temperature of the active layer of the sensor is stabilized to a value which corresponds to the desired air number at which the sensor is to react by heating coil 8. For example, as shown in FIG. 1, for an air number of $\lambda = 1.2$, the temperature would have to be 700° C. Only part of the exhaust gas stream passes through the inside of pipe 4. The actual amount is so chosen that the active layer is not cooled by the flow of gas. The resistance of the active layer is measured by measuring the resistance between electrodes 12 and 14 which are arranged in the axial direction on the active layer of the sensor. The resistance measurement can, for example, be carried out by a standard resistance bridge circuit whose output is applied to the input of an amplifier. The output of the amplifier then constitutes the sensor output signal.

The active layer consists of palladium together with a ceramic component. The ceramic component preserves the porous structure of the palladium and thereby effectively increases the specific surface area of the active layers. Preferably, the ceramic component is a material capable of mixed conductivity, that is mixed oxygen ion and electron conductivity. This type of material increases the exchange of oxygen between the active sensor material and the gas atmosphere because of its high oxygen permeability. For example, cerium dioxide with an addition of 0.5% by volume of niobium oxide to cause it to be electron conductive is suitable for this purpose.

FIG. 3 graphically illustrates how two sensors according to the present invention can be used to stabilize the air number $\lambda$ to a value $\lambda_O \pm \Delta\lambda$. The temperature $T_1$ of the first sensor is so adjusted that oxygen is given off at a value $\lambda_O - \Delta\lambda$. The temperature $T_2$ of sensor 2 is so adjusted that oxygen is given off for an air number $\lambda_O + \Delta\lambda$. In this way, the condition of the two sensors unambiguously defines the region $\lambda_O \pm \Delta\lambda$. Within the control region (indicated by shading) the first sensor is oxidized while the second sensor is reduced. Outside of the region, either both sensors are oxidized or both are reduced.

The two sensors are mounted in a common pipelet 6, one after the other in the axial direction. An individual heating coil 8 and temperature-responsive element 10 is provided for each sensor, as is an individual closed loop control system.

The closed loop control systems each have a reference input for adjusting the desired temperature, a signal input receiving the signal from temperature-responsive element 10 after suitable processing and an output furnishing the controlled current to the associated heating coil.

While the invention has been illustrated in preferred embodiments, it is not to be limited to the circuits and structures shown, since many variations thereof will be evident to one skilled in the art and are intended to be encompassed in the present invention as set forth in the following claims.

I claim:

1. Sensing means for furnishing an output signal indicative of a predetermined partial pressure of oxygen in exhaust gases corresponding to an air number ($\lambda$) exceeding 1 ($\lambda > 1$), said sensing means comprising
    a layer of metal changing state to the corresponding metal oxide or from said metal oxide to said metal at partial oxygen pressures varying in dependence on temperature for air numbers exceeding 1, said metal oxide having a low solubility in said metal, said change in state causing an abrupt change in electrical conductivity; and
    means connected to said layer for furnishing said output signal in response to said change in electrical conductivity.

2. Sensing means as set forth in claim 1, wherein said metal-metal oxide comprises palladium-palladium oxide.

3. Sensing means as set forth in claim 1, wherein said layer of metal or metal oxide constitutes an active layer; and
    wherein said active layer further comprises a ceramic component.

4. Sensing means as set forth in claim 3, wherein said ceramic component comprises cerium dioxide.

5. Sensing means as set forth in claim 4, wherein said cerium dioxide is doped with 0.5–10% by volume of $Nb_2O_5$.

6. Sensing means as set forth in claim 4, wherein said cerium dioxide is doped with 0.5–10% by volume of $Ta_2O_5$.

7. Sensing means as set forth in claim 1, wherein said air number is within an air number range of 1.05 to 1.4.

8. Apparatus for furnishing an output signal when the partial pressure of oxygen in a group of gases is a selected pressure within a predetermined pressure range, comprising
    sensing means having an active layer changing state from a metal to a metal oxide and from said metal oxide back to said metal at pressures of oxygen varying in dependence on temperature, said layer having an electrical conductivity undergoing a sudden change for each of said changes of state;
    means for maintaining said sensing means at a temperature selected within a predetermined temperature range, said temperature being selected so that said change of state occurs when said pressure of oxygen is said selected pressure; and
    means for sensing said change in conductivity and furnishing said output signal in response thereto.

9. Apparatus as set forth in claim 8, wherein said partial pressure range corresponds to air numbers in the range of 1.05 to 1.4.

10. Apparatus as set forth in claim 8, wherein said sensing means comprises a first and second sensor;
    wherein said means for maintaining said sensing means at said selected temperature comprises means for maintaining said first and second sensors at a first and second selected temperature, respectively, so that said change in said conductivity of said first and second sensors occurs at a partial pressure of oxygen respectively less than and exceeding said selected partial pressure by a predetermined incremental pressure.

11. Apparatus as set forth in claim 10, further comprising means for mounting said first and second sensors one following the other in the direction of flow of said gases; and
    wherein said temperature maintaining means comprises first and second measurement means for, respectively, measuring the temperature of said first and second sensor, first and second heating means for heating said first and second sensor, respectively, and control circuit means interconnected between said measurement means and said heating means for stabilizing the temperature of said first and second sensor means at said first and second selected temperature, respectively.

12. Apparatus as set forth in claim 11, wherein said mounting means comprises a pipe; and
    wherein said heating means comprises a first and second heating coil imbedded in said pipe.

* * * * *